United States Patent [19]

Appel et al.

[11] Patent Number: 5,017,375

[45] Date of Patent: May 21, 1991

[54] METHOD TO PREPARE A NEUROTROPHIC COMPOSITION

[75] Inventors: Stanley H. Appel; Yasuko Tomozawa, both of Houston, Tex.

[73] Assignee: Baylor College of Medicine, Houston, Tex.

[21] Appl. No.: 52,087

[22] Filed: May 18, 1987

Related U.S. Application Data

[60] Continuation-in-part of Ser. No. 768,887, Aug. 23, 1985, abandoned, which is a division of Ser. No. 444,293, Nov. 24, 1982, abandoned.

[51] Int. Cl.$^5$ ............... A61K 37/02; A61K 35/34
[52] U.S. Cl. ............... 424/570; 514/21; 530/300; 530/412; 530/416; 530/417; 530/427; 530/839; 435/70.3; 435/4
[58] Field of Search ............... 424/95; 435/68, 4; 514/21; 530/300, 412, 416, 417, 427, 839

[56] References Cited

U.S. PATENT DOCUMENTS 3,989,819 11/1976 Brockman ............... 424/95

FOREIGN PATENT DOCUMENTS 0082612 11/1982 European Pat. Off.
2420544 11/1979 France ............... 424/95
73526 4/1984 Japan ............... 530/839

OTHER PUBLICATIONS

Appel, Ann Neurol, 1981, 10:499–505.
Tomozawa and Appel, Society for Neuroscience Abstracts, No. 313.10, vol. II, Part 1; 15th Annual Meeting; Dallas, Texas 10/20/85.
Appel et al; Tropic Factors and Degenerative Neuroligic Disease, May 19–20, 1986, International Conference on Neuroplasticity, Madrid, Spain.
Tomozawa and Appel, Brain Research, 1986, 399:111–124.

Primary Examiner—Jacqueline M. Stone
Attorney, Agent, or Firm—Davis Hoxie Faithfull & Hapgood

[57] ABSTRACT

The present invention is based on the discovery that amyotrophic lateral sclerosis (ALS), Parkinson disease and Alzheimer disease are due to lack of a disorder-specific neurotrophic hormone or factor. Diagnosis is accomplished by assaying factors specific for a particular neuronal network or system; for example, dopamine neutotrophic hormones from striatum or caudate-putamen in the nigrostriatal dopaminergic neural system are used to diagnose and treat parkinsonism. With tissue culture, the presence or absence of spacific neurotrophic factos can be assessed in ALS, parkinsonism, and Alzheimer disease. If there is a deficiency, extracted and purified neurotrophic factors specific to the particular neuronal network or system can be injected into a patient having ALS, Alzheimer disease or parkinsonism for treatment of the disease.

17 Claims, 1 Drawing Sheet

METHOD TO PREPARE A NEUROTROPHIC COMPOSITION

CROSS-REFERENCE TO RELATED APPLICATIONS

The present application is a continuation-in-part of U.S. Ser. No. 768,887, filed 23 Aug. 1985, now abandoned, which is a divisional of U.S. Ser. No. 444,293, filed 24 Nov. 1982, now abandoned.

FIELD OF THE INVENTION

The field of the invention is the diagnosis and treatment of ALS. Parkinson's disease, and Alzheimer disease by neurotrophic factors.

BACKGROUND OF THE INVENTION

The causes of some of the most common and most devastating diseases of the nervous system remain unknown. Prominent on this list are amyotrophic lateral sclerosis (ALS), parkinsonism, and Alzheimer disease. Each of these conditions is presently considered to be a degenerative disorder of unknown origin. In each, viral or immunological causes have been suggested, but no convincing reproducible data support the presence of an infectious agent or a cell-mediated or humoral immune factor. All three diseases reflect pathological change in a relatively limited network within the peripheral or central nervous system, or both.

Amyotrophic Lateral Sclerosis

Amyotrophic lateral sclerosis is the name given to a complex of disorders the compromise upper and lower motor neurons. Patients may present with progressive spinal muscular atrophy, progressive bulbar palsy, primary material sclerosis, or a combination of the conditions. The majority of patients have components of all three types, but each form may represent the sole clinical manifestation of motor system involvement [1]. (Reference numbers are to references listed at the conclusion of the "Background of the Invention"). At the present time in the United States, the incidence of the combined disease is approximately 1.8 per 100,000 [2] and its prevalence is between 5 and 7 per 100,000. Males are affected more commonly than females, the ratio of males to females being 1.6:1. Approximately 10% of the cases are familial [3]. Onset may occur at any age but is most common in the later decades, and the incidence appears to increase with age. The mean age of onset is 66 years [6].

Distal weakness and atrophy are the hallmarks of the disorder, and both upper and lower motor neurons are affected. Sensory signs are usually absent. although quantitative sensory assessment by electromyography may indicate abnormalities [4]. The extraocular muscles and bladder are rarely involved. Progression usually occurs over 12 to 30 months, and death ensues as a result of severe impairment of breathing functions.

The major pathological abnormality is loss of large motor neurons of the motor cortex, brain stem, and spinal cord. In the remaining motor neurons there is chromatolysis and inclusions that are rich in ribonucleic acid or are Lewy body-like or eosinophilic (Bunina bodies) [5]. The whole neuron seems to be involved, and there is only minimal evidence of "dying back" of the peripheral axons [6]. In addition, large proximal axonal swellings (spheroids) have been reported in motor neurons from patients with ALS [7], and similar abnormalities can be induced in animals following injection of B-B'-iminodiproprionitrile, with resulting impairment of slow axonal transport [8]. These spheroids represent abnormalities of neurofilaments and may be found in the cytoplasm as well as in the axon.

Involvement of the motor system has been described in familial conditions appearing at earlier ages [3]. For example. Werdnig-Hoffman disease present in utero or in infancy as a rapidly progressive autosomal recessive condition characterized by severe weakness. Kugelberg-Welander disease is first seen in the juvenile period with weakness in the hips and subsequent involvement of the shoulder muscles. It is also inherited as an autosomal recessive disorder, although autosomal dominant and X-linked recessive transmission have been described. Both of these clinical conditions result from anterior horn cell abnormalities and share clinical features with the progressive muscular atrophies appearing later in life.

Parkinsonism

The presence of tremor, bradykinesia, and rigidity and loss of postural reflexes are characteristics of idiopathic parkinsonism. At the present time in the United States, the incidence of this disorder is estimated to be approximately 20 per 100,000, and its prevalence is 200 per 100,000 [9]. There is a slight male-to-female preponderance with the ratio of males to females being 1.2:1. The mean age of onset appears to be greater than 67 years and, as in ALS, the incidence may increase with age. As in ALS, some 5 to 10% of patients have a family history of the disorder.

The primary pathological abnormality appears to be loss of dopaminergic neurons in the substantia nigra. In addition, eosinophilic cytoplasmic inclusions termed Lewy bodies are present in nigral neurons. In cases of post-encephalitic parkinsonism, neurofibrillary alterations are noted in nigral neurons. The loss of these nigral cells leads to marked impairment in the nigrostriatal pathway and a great diminution in the dopaminergic synaptic input to the caudate and putamen. The enzymes of this incoming pathway that synthesize dopamine are impaired [10]. Of importance is the fact that no diminution is noted in the dopamine receptors within the striatum. In fact, enhancement of receptor sensitivity may well be present [11].

A number of pathological factors may impair nigrostriatal function and thus give rise to secondary parkinsonism. These include infections and post-infectious states; toxins such as manganese, carbon monoxide, or carbon disulfide; drugs including neuroleptic compounds such as phenothiazines, reserpine, and haloperidol; structural lesions such as brain tumors, trauma, or syrinx or vascular disease; as well as metabolic abnormalities such as hypoparathyroidism and basal ganglia calcification.

Alzheimer Disease

Alzheimer disease is a disorder of the later decades of life characterized by dementia. In clinical terms, it consists of a diffuse deterioration of mental function, primarily in thought and memory, and secondarily in feeling and conduct. Alzheimer disease has been used to designate dementia appearing before the age of 65 years. When the syndrome presents after that age, the term senile dementia of the Alzheimer type is used. In fact, it appears reasonable to consider both types as representing a single syndrome. The true incidence of the disorder is unknown, although recent data suggest that the incidence of all dementia in the U.S. population may be over 100 cases per 100,000, with its prevalence being over 550 per 100,000 [12]; Alzheimer disease probably affects at least 30 to 50% of patients with dementia, and in the United States there may be over one million individuals with severe dementia and several million more with mild to moderate dementia. It has been estimated that 1 out of every 6 persons over the age of 65 in the United States suffers from moderate dementia, and a majority of patients in the nursing home populations are affected with the disorder. The average age of onset is between 70 and 79 years, but without better information on the population at risk, a more accurate statement is not presently possible [12]. As in ALS and parkinsonism, the incidence of the syndrome clearly increases with advancing age. A family history of Alzheimer disease is present in 5 to 10% of the patients.

At the present time, the clinical diagnosis of Alzheimer disease is one of exclusion. Secondary causes of loss of memory and impaired cognitive function may result from multiple infarcts, leading to so-called multinfarct dementia, or from intracranial mass lesions such as subdural hematomas, brain tumors, or granulomas. Central nervous system infections of viral and bacterial origin, or even slow viral disorders such as Jakob-Creutzfeldt disease, are part of the differential diagnosis. Furthermore, metabolic disorders involving vitamin $B_{12}$ metabolism, thiamine or folate deficiency, thyroid dysfunction, hepatic and renal failure, as well as drug toxicity, may present as dementia. Nevertheless, when all these secondary causes, many of which are reversible, are eliminated, cerebral atrophy of unknown cause or Alzheimer disease still covers the largest number of patients. Elevations of aluminum content in the brain have been implicated in the pathogenesis of the disorder but appear to be secondary rather than primary [13, 14].

The pathological picture of Alzheimer disease has been well characterized over the years. It consists of senile plaques, which result from degeneration of nerve endings, and neurofibrillary tangles, which represent an alteration in the cytoskeletal apparatus [15]. In addition, intracellular cytoplasmic eosinophilic inclusions, termed Hirano bodies, are present, primarily in the hippocampus. Granulovacuolar degeneration is also noted. Senile plaques and neurofibrillary tangles in the brain are part of the "normal" aging process. However, at any age, patients with clinical Alzheimer disease appear to have much higher concentration of these abnormalities than do normal individuals [16].

The most recent prominent discovery in Alzheimer disease is a deficiency of the enzyme that synthesizes the neurotransmitter acetylcholine, namely, choline acetyltransferase (CAT) [17]. This deficiency is most marked in the cortex and hippocampus. Of note is the fact that acetylcholine receptors in the brain are either unaffected or relatively less affected. Thus, the defect in CAT reflects an alteration in the presynaptic cholinergic neuron. The diminution in CAT correlates with the presence of senile plaques: the greater the number of plaques, the lower the activity of CAT. Enzymes synthesizing several other neurotransmitters, including dopamine, norepinephrine, serotonin, and y-aminobutyric acid, as well as levels of vasoactive intestinal peptide, are all relatively unaffected compared to the loss of CAT activity. Somatostatin-like activity has recently been reported to be decreased in the cerebral cortex [18].

The CAT activity found in the hippocampus appears to derive largely from nerve terminals for which the cell of origin is in the septal nucleus. In addition, almost 70% of CAT activity in the cortex appears to reside in terminals with cell bodies located in the nucleus basalis of Meynert [19]. In rats, these cholinergic neurons lie intermingled with and beneath the medial globus pallidus, whereas in primates comparable cells are found exclusively outside the pallidum. In humans, the nucleus basalis of Meynert is situated in the fibrous zone beneath the globus pallidus and is a major component of the substantial innominata [20]. Thus, the cholinergic input to hippocampus and cortex may derive from a group of cells extending from the septal nuclei to constituents of the substantia innominata and may well be impaired in Alzheimer disease [20].

The following references are relevant to the invention

1. Munsat T. L., Bradley W. G.: Amyotrophic lateral sclerosis. In Tyler H. R., Dawson D. M. (eds): Current Neurology, vol 2. Boston, Houghton Mifflin, 1979
2. Juergens S. M., Kurland L. T., Okazaki H., Mulder D. W.: ALS in Rochester, Minn., 1925-1977. Neurology (NY) 30:463-470, 1980.
3. Engel W. K.: Motor neuron disorders. In Goldensohn E. S., Appel S. H. (eds): Scientific Approaches to Clinical Neurology. Philadelphia, Lea & Febiger, 1977, pp 1322-1346
4. Dyck P. J., Stevens J. C., Mulder D. W., et al: Frequency of nerve fiber degeneration of peripheral motor and sensory neurons in amyotrophic lateral sclerosis: morphometry of deep and superficial peroneal nerve. Neurology (Minneap) 25:781-785, 1975
5. Chou S. M.: Pathognomy of intraneuronal inclusion in ALS. In Tsubaki T, Toyokura Y (eds): Amyotrophic Lateral Sclerosis. Tokyo, University of Tokyo Press, 1979, pp 135-176
6. Bradley W. G., Kelemen J., Adelman L. S., et al: The absence of dying-back in the phrenic nerve of amyotrophic lateral sclerosis (ALS). Neurology (NY) 30:409, 1980
7. Carpenter S.: Proximal axonal enlargement in motor neuron disease. Neurology (Minneap) 18:841-851, 1968
8. Griffin J. W., Hoffman P. N., Clark A. W., Carrol P. T., Price D. L.: Slow axonal transport of neurofilament proteins: impairment of beta, beta-iminodipropionitrile administration. Science 202:633-635, 1978
9. Marttila R. J., Rinne U. K.: Changing epidemiology of Parkinson's disease: predicted effects of levodopa treatment. Acta Neurol Scan 59:80-87, 1979
10. Calne D. B., Kebabian J. Silbergeld E., et al: Advances in the neuropharmacology of parkinsonism. Ann Intern Med 90:219-229, 1979.
11. Burke R. E., Fahn S.: Movement Disorders. In Appel S. H. (ed): Current Neurology. New York, Wiley, 1981, vol 3, pp 92-137
12. Schoenberg B.: personal communication, 1981
13. Crapper D. R., Quittrat S., Krishnau S. S., Dalton A. J., DeBon U.: Intranuclear aluminum content in Alzheimer's disease, dialysis encephalopathy and experimental aluminum encephalopathy. Acta Neuropathol (Berl) 50:19-24, 1980
14. Perd D. P., Brody A. R.: Alzheimer's disease: x-ray spectrometric evidence of aluminum accumulation in neurofibrillary tangle-bearing neurons. Science 208:297-299, 1980
15. Terry R. D. Davies P.: Dementia of the Alzheimer type. Annu Rev Neurosci 3:77-95, 1980
16. Blessed G., Tomlinson B. E., Roth M.: The association between quantitative measures of dementia and of senile change in the cerebral grey matter of elderly subjects. Br. J. Psychiatry 114:797-811, 1968
17. Davies P., Maloney A. J. F.: Selective loss of central cholinergic neurons in Alzheimer's disease. Lancet 2:1403, 1976
18. Davies P., Katzman, R., Terry R. D.: Reduced somatostatin-like immunoreactivity in cerebral cortex from cases of Alzheimer's disease and Alzheimer senile dementia. Nature 288:279-280, 1980
19. Johnston M. V., McKinney M. Coyle J. F.: Evidence for a cholinergic projection to neocortex from neurons in basal forebrain. Proc Natl Acad Sci U.S.A. 76:5392-5396, 1979
20. Whitehouse P. J., Price D. L., Clark A. W., Coyle J. T., DeLong M. R.: Alzheimer disease: evidence for selective loss of cholinergic neurons in the nucleus basalis. Ann Neurol 10:122-126, 1981

The following additional references are also relevant to the invention:
Bottenstein J. E., Sato G. H.: Growth of a rat neuroblastoma cell line in serum-free supplemented media. Proc Natl Acad Sci U.S.A. 76:514-517, 1979
Bradshaw R. A.: Nerve growth factor. Annu Rev Biochem 47:191-216, 1978
Brown M. C., Holland R. L., Hopkins W. G.: Motor nerve sprouting. Annu Rev Neurosci 4:17-42, 1981
Cohen J. Levi-Montalcini R.: A nerve growth-stimulating factor isolated from snake venom. Proc Natl Acad Sci U.S.A. 42:571-574, 1956
Davies P.: Loss of choline acetyltransferase activity in normal aging and in senile dementia. Adv Exp Med Biol 113:251-257, 1978
Finch C. E.: Catecholamine metabolism in the brains of aging male mice. Brain Res 52:261-276, 1973
Fonnum F.: Radiochemical micro assays for the determination of choline acetyltransferase and acetycholinesterase activities. Biochem J. 115:465-472, 1969
Giller E. L., Neale J. H., Bullock P. N., Schrier B. K., Nelson P. G.: Choline acetyltransferase activity of spinal cord cell cultures increased by co-culture with muscle and by muscle-conditioned medium. J. Cell Biol 74:16-29, 1977
Hemmendinger L. M., Garber B. B., Hoffman P. C., Heller A.: Target neuron-specific process formation by embryonic mesencephalic dopamine neurons in vitro. Proc Natl Acad Sci U.S.A. 78:1264-1268, 1981
Hollyday M., Hamburger V.: Reduction of the naturally occurring motor neuron loss by enlargement of the periphery. J. Comp Neurol 170:311-320, 1976
Hudson A. J.: Amyotrophic lateral sclerosis and its association with dementia, parkinsonism and other neurological disorders: a review. Brain 104:217-247, 1980
Johnson D. A., Pilar G.: The release of acetylcholine from post-ganglionic cell bodies in response to depolarization. J. Physiol (Lond) 299:605-619, 1980
Mobley W. C., Server A. C., Ishii D. N., Riopelle R. J., Shooter E. M.: Nerve growth factor. N Engl J Med 297:1096-1104, 1977
Pestronk A., Drachman D. B., Griffin J. W.: Effects of aging on nerve sprouting and regeneration. Exp Neurol 70:65-82, 1980
Pittman R. W., Oppenheim R. W.: Neuromuscular blockage increases motoneurone arrival during normal cell death in the chick embryo. Nature 271:364-366, 1978
Prochiantz A., DiPorzio U., Kato A., Berger B., Glowinski J.: In vitro maturation of mesencephalic dopaminergic neurons from mouse embryos is enhanced in presence of their striatal target cells. Proc Natl Acad Sci U.S.A. 76:5387-5391, 1979
Reed D. M., Torres J. M., Brody J. A.: Amyotrophic lateral sclerosis and parkinsonian-dementia on Guam, 1945-1972. Am J Epidemiol 101:302-310, 1975
Smith R. G., Appel S. H.: Evidence for a skeletal muscle protein that enhances neuron survival, neurite extension, and acetylcholine (ACh) synthesis. Soc Neurosci Abstr 11:144, 1981
U.S. Pat. No. 4,294,818 discloses a diagnostic method for multiple sclerosis comprised of antibody preparations reactive with antigenic substances associated with lymphocytes.
U.S. Pat. No. 3,864,481 discloses a synthetic amino acid for suppression and diagnosis of multiple sclerosis.
U.S. Pat. Nos. 3,961,894; 4,046,870; and 4,225,576 disclose assay techniques for detecting hormones in the body.

SUMMARY OF THE INVENTION

The present invention is based upon the discovery that ALS, parkinsonism, and Alzheimer disease result from lack of a neurotrophic factor specific for a particular neuronal network or system which is elaborated or stored in the synaptic target of the affected neurons and exerts a specific effect by acting in a retrograde fashion. Diagnosis and treatment are based on neurotrophic factors which are extracted and tested in three different systems: in ALS the muscle factor which enhances motor neuron survival, growth and development; in parkinsonism the striatal factor which enhances substantial nigra survival, growth and development; and in Alzheimer disease the hippocampus factor which enhances septal neuron survival, growth and development. These neurotrophic factors are extracted, purified, and assayed. Diagnosis is accomplished for ALS by assaying motor neurotrophic factors from muscle in the motor system, for parkinsonism by assaying dopamine neurotrophic factors from striatum in the nigrostriatal system, and for Alzheimer disease the cholinergic neurotrophic factor released from the cortex and hippocampus. In case of deficiencies, neurotrophic factors specific to the particular neuronal network or system are injected into patients with ALS, parkinsonism and Alzheimer disease.

Accordingly, it is an object of the present invention to provide effective diagnosis and treatment of ALS, parkinsonism, and Alzheimer disease by neurotrophic factors.

It is a further object of the present invention to diagnose parkinsonism by determining or assaying the dopamine neurotrophic factor from striatum specific for the nigrostriatal system.

It is a further object of the present invention to treat parkinsonism by injecting neurotrophic factors specific to the nigrostriatal system.

A further object of the present invention is the extraction and purification of neurotrophic factors specific for the motor system, for the nigrostriatal system, and for cholinergic neurons of the nucleus basalis and septal nucleus.

Other and further objects, features and advantages of the invention are set forth throughout the specification and claims.

DESCRIPTION OF PRESENTLY PREFERRED EMBODIMENTS

Figure 1:
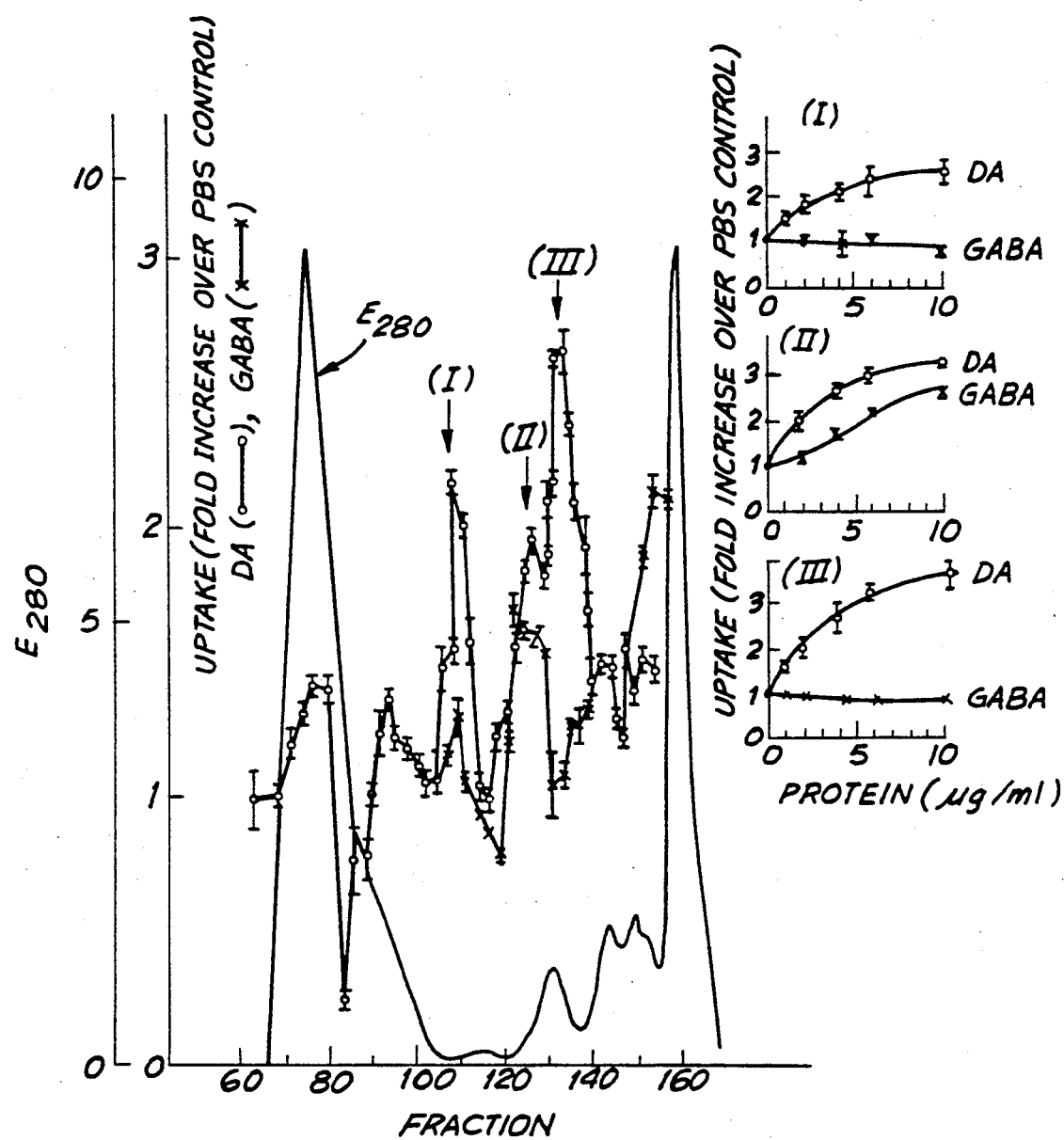
FIG. 1 shows the results of gel filtration chromatography of the striatal extract run on a Biogel P4 column as well as a dose response of the major fractions of the Biogel P4 column on the stimulation of high affinity dopamine and GABA uptake.

From the foregoing, all three diseases can be seen to represent disorders of specific neuronal networks; that is, the motor neuronal system, the nigrostriatal dopaminergic neuronal system and the cholinergic neuronal system. All reflect changes in a presynaptic neuronal input with secondary alterations of the target tissue. ALS represents pathological change in Betz cells, cranial motor neurons, and anterior horn cells; parkinsonism, in substantial nigra dopaminergic neurons; and Alzheimer disease, in the cholinergic input from nucleus basalis and septal neurons to cortex and hippocampus, respectively.

The role of neurotrophic hormones of the present invention is a modification of the notion of intrinsic aging of selected neurons; that is, the presence of specific extrinsic factors influence the maintenance and survival of neurons. In each disease, the system degeneration is due to diminished availability of a specific neurotrophic hormone normally released by the post-synaptic cell, taken up by the presynaptic terminal, and exerting its effect by retrograde transport up the presynaptic axon to the soma and nucleus.

For each of these three neuronal systems, neurotrophic factors can be demonstrated in vitro which enhance neuron survival, promotes neurite extension, and increase the activity of the neurotransmitter synthetic enzymes in the innervating cell. The same factors responsible for survival of neurons in vitro may also be responsible for survival of neurons in vivo. Similar or even the same factors may also be responsible for maintenance of neurons throughout the life cycle in vivo, and may decrease as a normal function of aging.

Thus, a primary manifestation of ALS, Parkinson disease, or Alzheimer disease is failure of the target tissue to supply the necessary neurotrophic hormone. Marked pathological change in the tissue need not be present. Impaired synthesis or release (or both) of the relevant hormone would represent the sine qua non of disease. For example, in the lower motor neuron syndromes of ALS, failure of muscle cells to release the appropriate motor neurotrophic hormone would result in failure of anterior horn cells. The pathological picture would be one of gradual cessation of anterior horn cell function with chromatolysis and of altered nuclear function with minimal evidence of "dying back." Similarly, impairment of Betz cells would result from decreased release of neurotrophic hormone from target neurons. A more precise statement is not possible for the upper motor neuron syndrome since the synaptic target of the descending Betz cell axon is not known with certainty in humans.

In parkinsonism, the neurotrophic failure would be characterized by inability of striatal cells to provide the required dopamine neurotrophic hormone. In Alzheimer disease, the failure would be in hippocampus and cortical cells to supply the relevant cholinergic neurotrophic hormone. Thus, in each system, the lack of an appropriate hormone released from post-synaptic cells impairs the viability of the presynaptic cells. Anterior horn cells, Betz cells, substantia nigra cells, and septal and basal nuclei undergo gradual deterioration.

Thus, motor neurotrophic hormones are released from muscle and are specific for the motor system, dopamine neurotrophic hormones are released from the striatum and are specific for the nigrostriatal dopaminergic system, and cholinergic neurotrophic hormones are released from the cortex and hippocampus and are specific for cholinergic neurons of the nucleus basalis and septal nucleus. With the availability of tissue culture, the presence, deficiency, or absence of specific neurotrophic hormones can be assessed in ALS, parkinsonism, and Alzheimer disease readily and easily.

The present invention discloses a method to prepare a composition effective in treating Parkinson's disease comprising:

(a) extracting factors from the caudate-putamen tissue of a normal mammal; and (b) assaying the caudate-putamen extract for trophic effects on dopaminergic neurons obtained from substantia nigra.

The method of the present invention further comprises the isolation of three factors with the following molecular weight ranges: 1800-2600 daltons (Factor I); 1500-1800 daltons (Factor II); and 1000-1600 daltons (Factor III). The molecular weight ranges of the factors described herein have been determined in solution by gel filtration chromatography and thus, have been given in ranges since the specific molecular weight may vary according to the procedure used to isolate each factor.

The tissue extract used in the present invention is derived from either striatum tissue from rat or caudate and putamen tissue from bovine sources. The tissue sample is derived from those regions of the brain innervated by dopaminergic neurons of the substantia nigra, such as the striatum and the caudate-putamen, which are rich in dopaminergic neurotrophic factors. Significant amounts of dopaminergic neurotrophic activity can be obtained in extracts of the striatum, the hippocampus-entorhinal cortex-amygdaloid cortex area and the cerebral cortex. The precise region of the brain used is dependent upon the type of mammal used as the source of tissue. For example, in the rat, the preferred tissue is striatum whereas preferred bovine midbrain tissue are the caudate and putamen. Both the striatal tissue and the caudate-putamen tissues are regions of the brain innervated by dopaminergic neurons of the substantia nigra.

By "trophic effects" it is meant that the extracted neurotrophic factors have selective effects on specific neural elements, said effects contributing to the survival, growth, maturation, differentiation, and regeneration of neurons present in the nervous tissue.

Biological assays for neurotrophic factors active on either dopaminergic neurons or GABAergic (gamma alpha aminobutyric acid containing) neurons are used as one means of demonstrating the trophic effects possessed by the present neurotrophic factors. Dopaminergic activity is usually defined as the ability to stimulate specific high affinity $^3$H-dopamine uptake by dopaminergic neurons. In accord, GABAergic activity is the ability to stimulate high affinity $^3$H-GABA uptake by GABAergic neurons. Both of these assays were conducted because the substantia nigra in the mesencephalon contains dopaminergic and GABAergic neuronal populations.

Very generally, the trophic factors which exhibit trophic effects on dopaminergic neurons can be isolated from caudate and putamen tissues from human or bovine sources or striatal tissue from rat. Thus, the source of tissue can be taken from a variety of normal mammals. The use of the term "striatal" and "caudete-putamen" herein refers to the regions of the brain innervated by dopaminergic neurons of the substantia nigra, regardless of tissue source.

The neurotrophic factors described herein can be isolated using a variety of conventional and well-known extraction and purification procedures. Extraction procedures include homogenizing the tissue in an aqueous solution using a blender or laboratory homogenizer. The aqueous solution is usually buffered to physiological salt and pH and may contain one or more protease inhibitors including one or more reducing agents and one or more chelating agents. The particular buffers, reducing agents, and protease inhibitors used in the extraction step are not critical to practice the present invention; thus, the following reagents are merely illustrative of the reagents which might be utilized. For example, the aqueous solution may include phosphate-buffered saline solution (PBS), citrate-phosphate buffer; protease inhibitors may include trypsin inhibitor, phenylmethylsulfonyl fluoride (PMSF), pepstatin A, and leupeptin; chelating agents may include EDTA, EGTA and the like; and reducing agents may include β-mercaptoethanol, dithiothreitol, and the like. The factors described in these examples are stable at moderate acid and basic pHs. Therefore, extraction could be in acidic or basic aqueous solutions such as acetic acid or ethanolamine solutions. A preferred embodiment of the present invention utilizes PBS, pH 7.4, supplemented with soybean trypsin inhibitor and β-mercaptoethanol to extract the dopamine neurotrophic factors. Tissue extracts prepared by this tissue homogenization are then clarified by centrifugation.

The recovery of Factor I is particularly dependent on the freshness of the tissue used in the extraction process. In general, it is best to use tissue from 6–12 month old calves. Thus, Factor I may be recovered in greater yield if the tissue is from a 6 month old calf and is removed from the calf less than two hours prior to the extraction protocol. In addition, if a trypsin inhibitor and β-mercaptoethanol are not present in the buffer used for extraction, recovery of Factor I is greatly reduced.

Several fractionation procedures which can be used singly or in combination to increase purity of a composition are well known in the art. These include: size fractionation using molecular sieve (or gel filtration) chromatography, ion exchange chromatography under suitable conditions; affinity chromatography using for example, antibodies directed to the biologically active form of the neurotrophic factor; absorption chromatography using non-specific supports, such as hydroxyapatite, silica, alumina, and so forth; and also gel supported electrophresis. A detailed description of the procedures used to purify the present neurotrophic factors is described in the examples below.

Since the factors described herein are relatively small (<3,000 daltons), undesired proteins and cellular debris can be removed by ultrafiltration of the extract through an appropriate filter, for example, an Amicon YM10 filter. Alternatively, and preferably, the extracted dopamine neurotrophic factors may be directly purified by gel filtration chromatography using an appropriate matrix to resolve proteins having molecular weights less than 3,000 daltons. The matrix, such as a Biogel P4 column, is preequilibrated or equilibrated with an appropriate buffer such as 25 mM ammonium bicarbonate, pH 6.5, which is also useful to elute the neurotrophic factors.

Dopamine uptake stimulating activity is separated into three peaks of activity under gel filtration chromatography. The peak with the highest molecular weight (~1800–2600 daltons) was designated Factor I; Factor II (~1500–1800 daltons) elutes consistently just in front of Factor III (~1000–1600 daltons).

The factors in these three active peaks were assayed for enhancement and differentiation of dopaminergic neurons. Mesencephalon tissue is obtained from mammalian species for the assay. It is preferred to use mesencephalic cells from E14 rat embryos either for dissociated cell culture or tissue explant culture.

Several different assays may be performed to determine the nature and specificity of the effects of the factors on the dopaminergic neurons in these cultures. These include effects on survival, cell growth, neuronal process outgrowth, and general stimulation of metabolic functions including those specifically related to neuronal type. For example, enhancement of levels of enzymes such as tyrosine hydroxylase which are involved in this transmitter synthesis may be determined. The preferred method of assay is to incubate cultures of rat dopaminergic neurons with or without each of the neurotrophic factors for several days after which specific effects on the dopaminergic neurons are determined. Usually, high affinity dopamine uptake is measured by incubating treated cultures with $^3$H-dopamine for 80 min at 22° C. Appropriate controls allow determination of the ability of each factor to specifically stimulate high affinity dopamine uptake. Dopaminergic neurons can be identified in cultures by staining for dopamine by glyoxylic acid-induced catecholamine histofluorescence.

Besides dopaminergic neurons, mesencephalon cultures contain large amounts of GABAergic (gamma-aminobutyric acid containing) neurons. Therefore, one way of determining neurotrophic specificity for dopaminergic neurons is by the assaying for the effect of each factor on high affinity GABA uptake which is carried out in a similar fashion using $^3$H-γ-aminobutyric acid. Factors (e.g., Factor II) which stimulate GABA uptake are not dopaminergic specific, while only those factors (e.g., Factors I and III) which stimulate dopamine uptake and do not stimulate GABA uptake are dopaminergic specific. The lack of tight specificity of Factor II for dopaminergic neurons does not preclude its utility, since trophic factors with broad spectrum of action may also be effective in treating Parkinson's disease.

The present neurotrophic factors may be further purified by ion-exchange chromatography. The fractions corresponding to the Factor III isolate can be purified away from any contaminating Factor II component by anion-exchange high performance liquid chromatography (HPLC). The Factor III eluate is dissolved in a low salt buffer and adjusted to pH ~7.0.

Usually, a low salt phosphate buffer such as 10 mM $NaH_2PO_4$-$Na_2HPO_4$ is used. This solution is adsorbed to an anion exchange HPLC column such as DEAE-5-PW-equilibrated with a similar buffer. This column is eluted isocratically for a time and then with a linear gradient of NaCl from 0 to 250 mM. The Factor III neurotrophic activity elutes between 50-60 mM NaCl whereas the Factor II neurotrophic activity elutes around 140 mM NaCl.

The Factor I activity can be purified by cation-exchange HPLC by dissolving the Factor I eluate in a low salt phosphate buffer and adjusting the pH to 4.5. The resulting solution is applied to a cation exchange (e.g., SP-5-PW) HPLC column preequilibrated or equilibrated with 10 mM phosphate buffer, pH 4.5. After washing thoroughly, the desired factor is isocratically eluted with the pH 4.5 phosphate buffer for five minutes and then eluted in a linear gradient at 0 to 250 mM NaCl. The Factor I neurotrophic activity elutes between 50-60 mM NaCl.

Each of the factors isolated above may be subjected to further purification protocols and assayed for dopaminergic activity as described hereinabove. However, the individual factors isolated according to the procedures described in the following examples have been characterized sufficiently to determine their ability to enhance process growth and specific dopamine uptake in mesencephalon cultures.

Extracts of the striatum of the mammalian brain influence the survival, development and differentiation of substantia nigral dopaminergic neurons. The importance of this isolation and purification is that such a factor may not only play a role in the development of dopaminergic innervation during development, but it may also play a role in maintenance of such innervation. Thus, in diseases such as Parkinson's disorder in which substantia nigra cells are lost, such a dopaminergic neurotrophic factor may be deficient. Replacement of this particular neurotrophic hormone may have salutary effects on the clinical syndrome of Parkinson's disease.

Accordingly, the invention further comprises a method of diagnosing the presence of Parkinson's disease in a subject by detecting a deficiency of specific neurotrophic functional effects in said subject as compared to normal controls, wherein said deficiency is detected by the method which comprises:

(a) extracting a component from the caudate-putamen tissue of said subject;

(b) assaying said extract for neurotrophic activity with respect to the neuronal system normally associated with said caudate-putamen; and (c) comparing said neurotrophic activity to activity exhibited in the same assay by similar extracts from caudate-putamen tissue of controls.

The component may be prepared as described in the following examples and assayed for dopaminergic activity in the nigrostriatal pathway. If a deficiency in dopaminergic neurotrophic hormone levels is identified, treatment may be accomplished by injecting the present factors.

The factors prepared as described herein are suitable for parenteral administration to humans or other mammals in therapeutically effective amounts (e.g., amounts which eliminate or reduce the patient's pathological condition) to provide therapy for Parkinson's disease.

Additionally, the factors may be useful in transplant therapy as they will have a supportive effect on survival and maintenance of dopaminergic tissues or cells transplanted to the Parkinsonian brain in order to replace the lost dopaminergic function.

The formulations of this invention are useful for parenteral administration, for example, intravenous, subcutaneous, intramuscular, intraorbital, opthalmic, intracapsular, intraspinal, intrasternal, topical, intranasal aerosol, scarification, and also, for oral administration. The preferred route of administration would be by intranasal aerosol.

The concentration of neurotrophic factor in a therapeutic composition will vary depending on a number of factors, including the dosage of the drug to be administered, and the chemical characteristics, e.g., hydrophobicity, of the factor. Generally, the factor is provided in an aqueous physiological buffer solution containing about 0.1 to 10% w/v factor. Other adjuvants include glycocholate, deoxycholate and sodium tauroglycocholate.

The invention is further described by the following examples. These examples are not intended to limit the invention in any manner.

EXAMPLE 1

Purification of Dopaminergic Factors

A. Extraction

About 30 g of 6 month old calf caudate-putamen tissue on ice was homogenized in five volumes (wt/vol) of PBS (⅓ of normal PBS, pH 7.0) in the presence of 0.1 mg/ml soybean trypsin inhibitor and 0.5 mM beta-mercaptoethanol and allowed to stand for 30 min on ice. The extract was prepared by centrifugation of the PBS homogenate at 100,000 g for 90 min. The extraction was repeated one more time under the same conditions and the resulting supernatant filtered through a 2 micron filter, lyophilized, and assayed for trophic activity as described in Example 2.

B. Gel Filtration Chromatography

The lyophilized PBS extract was dissolved in 8 ml distilled water containing 0.5 mM beta-mercaptoethanol and 0.1 mg/ml trypsin inhibitor. This suspension was applied to a Biogel P4 (BioRad) molecular sieving column preequilibrated with 25 mM ammonium bicarbonate buffer, pH 6.5. Fractions were collected and protein concentrations were assessed by a modification of the method of Lowry (Schacterle and Pollack, *Anal Biochem* (1973) 51: 654-655). The collected fractions were also assayed for stimulation of high affinity dopamine uptake and neuronal high affinity GABA uptake as described below. Three peaks of stimulatory activity of high affinity of dopamine uptake were observed which correspond to the following approximate molecular weights: 1800-2600 daltons (Factor I); 1500-1800 daltons (Factor II); and 1000-1600 daltons (Factor III). The peak with the highest molecular weight, Factor I, appears to be quite sensitive to protease activity. The presence of this peak is variable and is dependent on the age and freshness of calf brain tissue.

The stimulatory effects of these three active peaks on high affinity dopamine uptake and neuronal high affinity GABA uptake were compared and the results are shown in FIG. 1. Factors I and III stimulate high neuronal high affinity dopamine uptake in dose-dependent manner, but do not stimulate neuronal high affinity GABA uptake. Factor II, in contrast, stimulates both high affinity dopamine uptake and neuronal high affinity GABA uptake. Therefore, Factor I and Factor III appear to be specific for dopaminergic neurons while Factor II is less specific being neurotrophic for both dopaminergic and GABAergic neurons in dissociated mesencephalon cultures.

C. Anion-Exchange HPLC Chromatography of Factor III

The Biogel P4-Factor III fractions, including some overlapped areas of Factor II, were lyophilized and dissolved in 2 ml phosphate buffer (10 mM $NaH_2PO_4$-$Na_2HPO_4$, pH 7.0). Factor III was applied to a preequilibrated (with the same phosphate buffer) DEAE-PW-HPLC column (7.5 mm×7.5 cm, Waters Associates). The column was eluted isocratically for 20 min, and then with a linear gradient of NaCl from 0 to 250 mM in the phosphate buffer at a flow rate of 0.5 ml/min. A peak of dopaminergic stimulating activity eluted at 50-60 mM NaCl. As shown in FIG. 1, this fraction stimulated high affinity dopamine uptake, but not neuronal high affinity GABA uptake. A second peak of activity eluted at 140 mM NaCl. This peak, however, stimulated both dopamine and GABA uptake and is therefore Factor II. Thus, dopaminergic Factor III can be effectively separated from Factor II by DEAE chromatography resulting in a purification of approximately 5,000-6,000 fold purification over the activity in the crude extract. Correspondingly, Factor II may be isolated by pooling fractions from the P4 chromatography step which contain Factor II plus some overlap of Factor III and similarly subjecting the pooled fractions to anion-exchange chromatography. A summary of purification results for Factor III is provided in Table 1 below.

TABLE 1

| | PURIFICATION OF FACTOR III ACTIVITY | | | |
|---|---|---|---|---|
| FRACTION | PROTEIN (mg) | SA (U/mg) | UNITS | Ka |
| 100,000 xg SPN | 728 ± 42 | 25 | 18360 ± 2440 | 153 μg/ml ± 15 × $10^3$ |
| P4 (III) DEAE (50-60 mM Pool) | 24 ± 5 | 508 | 12200 ± 1700 | 5 μg/ml ± 0.8 × $10^3$ 30 ng/ml ± 12 |

D. Cation-Exchange HPLC Chromatography of Factor I

The Biogel P4-Factor I fractions were dissolved in 1 ml phosphate buffer (10 mM $NaH_2PO_4$-$Na_2HPO_4$, pH 4.5) and applied to a preequilibrated (with the same phosphate buffer) SP-5-PW HPLC column (7.7 mm×7.5 cm, Waters Associates). Bound material was isocratically eluted with the pH 4.5 phosphate buffer for 5 min, and then eluted in an increasing linear gradient of NaCl from 0 to 250 mM. A peak of dopaminergic stimulating activity eluted at 50-60 mM NaCl. This dopaminergic factor, Factor I, was purified 6,500 fold over the activity in the crude extract at the stage of SP-5-PW HPLC.

EXAMPLE 2

Assay Methods

A. Tissue Cultures

Explant and dissociation cultures of the substantia nigra were obtained from 14-day-old rat embryos. At this stage of development, the dopaminergic neurons in the mesencephalon are predominantly postmitotic, but have not yet innervated their striatal target. Synthesis of dopamine was detected by histofluorescence using the procedure by Specht et al (*J Comp Neurol* (1981) 199: 233-253; ibid 255-276). For explant cultures, the mesencephalon was dissected out and the ventral region fragment was dissected into 0.3 to 0.4 mm pieces in the culture medium. Thirty to forty pieces were cultured on poly-L-lysine (Sigma, 3,000,000 M.W. polymerization) coated 35 mm Falcon tissue culture plates in a standard culture medium consisting of 50% high glucose DMEM-50% F12 supplemented with insulin (5 μg/ml), transferrin (100 μg/ml), progesterone (20 nM), putrescine (100 μM), selenium (30 nM), glutamine (4 mM), gentamycin (50 μg/ml) and HEPES (5 mM) (Bottenstein and Sato, *Proc. Natl Acad Sci U.S.A.* (1979) 76: 514-518) without serum and maintained at 37° C. in a 95% air-5% $CO_2$ humidified incubator. Dissociation cultures were prepared by triturating mesencephalic cells in the presence of DNase (1 mg/ml, Sigma) and trypsin (0.2 mg/ml, Sigma) (McCarthy and de Vellis, *J Cell Biol* (1980) 85: 890-902). After washing twice with culture medium containing 4% heat inactivated horse serum, cells were plated at 100,000 cells/well on the poly-L-lysine coated Falcon 96 multiwell plates in the same culture medium. Six hours after plating, the soluble factors were applied onto the medium with cytosine arabinoside (2 μM) and the cells were cultured for three days total in a 95% air-5% $CO_2$ humidified incubator.

B. Dopaminergic Activity

Assays of high affinity $^3$H-dopamine uptake were performed by the method reported by Prochiantz et al, *Nature* (1981) 293: 570-572. Cells were incubated at 22° C. for 80 min with 50 nM H-dopamine (New England Nuclear, 20-30 Ci/mmole) in 150 ul of PBS containing 6 mg/ml glucose, 1 mg/ml BSA, and 40 ug/ml ascorbic acid, pH 7.0 in the presence of pargyline (100 μM), an inhibitor of monoamine oxidase. The assays were terminated by washing cells four times with ice-cold PBS without $CaCl_2$ and $MgCl_2$. Cells were lysed by addition of 150 ml of 0.5N NaOH for 2 hours at room temperature. Incorporated $^3$H-dopamine was measured by a liquid scintillation counter. $^3$H-dopamine uptake by dopaminergic neurons was verified by specific inhibition by benztropine and desmethylimpramine at 1 μM (Prochiantz et al, 1981, supra). In the presence of both inhibitors the high affinity dopamine uptake in these experiments was inhibited by 87%. To determine the non-specific dopamine uptake, dissociated cells, enriched in glia, were prepared from 1-day-old rat cerebral cortex, and cultured at the similar cell density. The population was 98% glia by GFAP staining. Dopamine uptake in this culture was less than 3% of the PBS control of mesencephalon cultures.

C. GABAergic Activity

The major neuronal constituents in mesencephalon cultures are dopaminergic and GABAergic neurons. The striatal factors were, therefore, tested for their ability to enhance high affinity GABA uptake. Mesencephalic cells were incubated at 22° C. for 80 minutes with 100 nM $^3$H-γ-aminobutyric acid (GABA) (ICN, 75

Ci/mmole) in PBS, pH 7.4, in the presence of β-alanine (2 mM), an inhibitor of glial low affinity GABA uptake. High affinity $^3$H-GABA uptake specific for GABAergic neurons was verified with respect to Factor II, with the inhibitor L-2, 4-diaminobutyric acid (1 mM) (Pastuszko et al, *Proc Natl Acad Sci U.S.A.* (1981) 78: 1242–1244).

D. Catecholamine Histofluorescence

Dissociated cultured mesencephalon cells were analyzed by catecholamine fluorescence using a glyoxylic acid technique (Sumners et al, *Brain Res* (1983) 264: 267–275). Cells grown on glass multichamber slides were rinsed in ice-cold PBS, pH 7.4, and immediately placed in a 1% buffered glyoxylic acid solution (1% glyoxylic acid, 0.1M phosphate, pH was adjusted to pH 7.4 with NaOH 4° C.) for 5 minutes. Excess glyoxylic acid solution was removed. Slides were dried for 5 minutes under warm air, and then heated for 10 minutes at 95° C. Fluorescence was viewed under a Nikon fluorescence microscope with V filter block (IF 399–425 interference excitation filter and 470 barrier filter). Control cells were treated with cold PBS for the same period. To intensify dopamine histofluorescence, cells were pretreated 5 hours with 100 μM L-Dopa in 100 μg/ml ascorbic acid and 100 μM pargyline. Non-dopaminergic neurons and glial cells did not show any specific glyoxylic acid induced-catecholamine fluorescence under these conditions.

We claim:

1. A method to prepare a neurotrophic composition, which method comprises:
   (a) extracting factors from caudate-putamen tissue of a normal mammal;
   (b) assaying the caudate-putamen extract for trophic effects on dopaminergic neurons obtained from substantia nigra as measured by the ability to stimulate dopamine uptake by said neurons; and
   (c) isolating factors having said trophic effects.

2. The method of claim 1 wherein said normal mammal is of bovine source.

3. The method of claim 1 wherein said extraction comprises homogenizing the tissue extract in aqueous solution, centrifuging the homogenate, and recovering the supernatant.

4. The method of claim 1 which further comprises purifying the isolated factors by fractionation.

5. The method of claim 4 wherein said purification yields dopaminergic neurotrophic factors having molecular weights less than 3,000 daltons.

6. The method of claim 5 wherein a dopaminergic neurotrophic factor has a molecular weight range of about 1,000 to about 1,600 daltons.

7. The method of claim 5 wherein a dopaminergic neurotrophic factor has a molecular weight range of about 1,500 to about 1,800 daltons.

8. The method of claim 5 which further comprises purifying the dopaminergic neurotrophic factor by cation-exchange HPLC chromatography.

9. The method of claim 3 wherein said tissue extract is prepared from fresh tissue and said aqueous solution comprises a buffer supplemented with one or more protease inhibitors.

10. The method of claim 9 which further comprises purifying said isolated factors by gel filtration chromatography.

11. The method of claim 10 wherein said purification yields dopaminergic neurotrophic factors having molecular weights less than 3,000 daltons.

12. The method of claim 5 wherein a dopaminergic neurotrophic factor has a molecular weight range of about 1,800 to about 2,600 daltons.

13. The method of claim 11 wherein a dopaminergic neurotrophic factor has a molecular weight range of about 1,500 to about 1,800 daltons.

14. The method of claim 11 wherein a dopaminergic neurotrophic factor has a molecular weight range of about 1,000 to about 1,600 daltons.

15. The method of claim 11 wherein said purification further comprises purifying the dopaminergic neurotrophic factors by anion-exchange HPLC chromatography.

16. A factor prepared by the method of claim 7.

17. A factor prepared by the method of claim 12.

* * * * *